United States Patent
Penco

(10) Patent No.: US 6,887,883 B2
(45) Date of Patent: May 3, 2005

(54) USE OF NATURAL CHRYSANTHONE COMPOUNDS HAVING ANTIANGIOGENIC ACTIVITY

(75) Inventor: Sergio Penco, Milan (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 119 days.

(21) Appl. No.: 10/220,184

(22) PCT Filed: Mar. 12, 2001

(86) PCT No.: PCT/IT01/00120

§ 371 (c)(1),
(2), (4) Date: Nov. 6, 2002

(87) PCT Pub. No.: WO01/68071

PCT Pub. Date: Sep. 20, 2001

(65) Prior Publication Data

US 2003/0149068 A1 Aug. 7, 2003

(30) Foreign Application Priority Data

Mar. 13, 2000 (IT) ................ RM2000A000128

(51) Int. Cl.⁷ ................ A61K 31/44; A61K 31/35
(52) U.S. Cl. ................ 514/290; 514/454
(58) Field of Search ................ 514/290, 454

(56) References Cited

U.S. PATENT DOCUMENTS 5,843,755 A    12/1998   Obayashi et al.

FOREIGN PATENT DOCUMENTS

WO    00/03726    1/2000

OTHER PUBLICATIONS

Albinati et al, "Chrysanthone A Bioactive Alkaloid from Ascochyta–Chrysanthemi" PHYTOCHEMISTRY, vol. 28, No. 3, 1989, pp. 923–928.

Arnone et al, "Chrysanthones B and C Secondary Metabolites Produced by the Fugus Ascochyta–Chrysanthemi", PHYTOCHEMISTRY, vol. 29, No. 8, 1990, pp. 2499–2502.

Assante et al, "Bioactive Secondary Metabolites from Some Mycosphaerella spp", Rivista di Patologia Vegetale, vol. 4, No. 1, 1994, pp. 25–38.

Coval et al, "Pyrenoline A and B Two New Phytotoxins from Pyrenophora–Teres", Tetrahedron Letters, vol. 31, No. 15, 1990, pp. 2117–2120.

*Primary Examiner*—Rebecca Cook
(74) *Attorney, Agent, or Firm*—Nixon & Vanderhye P.C.

(57) ABSTRACT

A series of compounds of natural origin are described, as useful agents for the treatment of diseases characterised by abnormal angiogenesis. These compounds are: chrysanthone A having formula (I); chrysanthone B having formula (II); and chrysanthone C having formula (III).

8 Claims, No Drawings

USE OF NATURAL CHRYSANTHONE COMPOUNDS HAVING ANTIANGIOGENIC ACTIVITY

This application is the US national phase of international application PCT/IT01/00120 filed 12 Mar. 2001 which designated the U.S.

The invention described herein relates to the use of compounds of natural origin for the treatment of diseases associated with abnormal angiogenesis.

Angiogenesis in the adult is normally quiescent, but it represents a normal function, for example, in the healing of wounds, or in the reconstruction of the endometrium during the female reproductive cycle.

The angiogenic response is physiologically stimulated when the vascular functions are reduced and tissue perfusion is inadequate.

More generally, it can be claimed that, in physiological conditions, angiogenesis constitutes a positive feedback in response to inadequate perfusion, or to a reduced supply of oxygen and nutrients, such as occurs, for instance, in the case of occlusion of an artery, in situations of tissue mass growth (for example, the neovascularisation that accompanies the formation of muscle tissue); and in the case of an increased work load in association with an increased oxygen and nutrient requirement.

In the course of local ischaemia, due to partial or complete occlusion of an artery, the development of collateral vessels is necessary in order to maintain perfusion.

The normal process of angiogenesis is modulated by the equilibrium between pro-angiogenic molecules such as fibroblast growth factor (FGF), placental growth factor, vascular endothelial growth factor (VEGF), transforming growth factor (TGF), angiogenin, interleukin-8, and hepatocyte growth factor, and negative angiogenesis regulators such as thrombospondin-1, angiostatin, alpha interferon, prolactin 16-Kd fragment, inhibitors of metallo-proteinases (MMPS), platelet factor 4, and genisteine.

It is well known that the growth of a primary tumour is favoured by good vascularisation of the tumour tissue. An adequate supply of oxygen and nutrients promotes rapid growth of the tumour itself.

It has been demonstrated that the extent of angiogenesis can be an extremely negative factor in the prognosis of neoplasms (van Hinsbergh V W, Collen A, Koolwijk P; Ann. Oncol., 10 Suppl., 4:60–3, 1999; Buolamwini J K; Curr., Opin., Chem., Biol., 3(4):500–9, 1999 August).

It is also known, in the neoplastic field, that a fundamental stage in the biology of the tumour cell is the acquisition of metastasising capability.

The tumour cells that metastasise are able to lose adherence to the surrounding structures, invade blood and lymphatic vessels and colonise other tissues at a distance where they continue to reproduce themselves.

Metastasising is also a critical event in the clinical history of the disease, being the main cause of death due to cancer. It is closely associated with and facilitated by the presence of vascular tissue in the tumour site or adjacent areas.

The migration of tumour cells across the surrounding structures enables the cells to reach the intratumoural blood vessels, whether pre-existing or formed by neoangiogenesis, and thus reach the bloodstream (Ray J M., Stetler-Stevenson W G; Eur. Respir. J., 7(11):2062–72, 1994; Stetler-Stevenson W G, Liotta L A, Kleiner D E Jr; FASEB J., 7(15):1434–41, 1993 December.

The presence of communication between lymphatic and blood vessels in the vascular district of the tumour enables the neoplastic cells to move in both vascular systems.

Recent studies have shown a direct relationship between angiogenesis and arthritic disease (Koch A E; Arthritis and Rheumatism 41:951–962, 1998). In particular, it has been demonstrated that neovascularisation of the articular cartilages plays a crucial role in pannus formation and in progression of arthritis. A normal cartilage does not possess blood vessels, while the synovial fluid of arthritic patients contains an angiogenesis-stimulating factor produced by endothelial cells (EASF).

The presence of this factor is associated with vascularisation and degradation of the cartilage.

Other diseases are also related to abnormal angiogenesis.

It has been found that, in diabetic retinopathy [Histol Histopathol 1999 October; 14(4):1287–94], psoriasis [Br. J. Dermatol. 1999 December; 141(6):1054–60], chronic inflammation and atherosclerosis [Planta Med 1998 December; 64(8):686–95], neovascularisation of the affected tissues is a facilitating factor.

The control of neovascularisation is therefore one of the basic elements for the control and cure of these diseases.

Compounds of natural origin with an antiangiogenic activity useful in human therapy are already known. For example, fumagillin, a compound extracted from the fungus *Aspergillus fumigatus*, presents substantial antiangiogenic capability. Its synthetic derivative, TNP-470, is in the clinical experimentation stage for the treatment of tumours (Griffith E C, Proc. Natl. Acad. Sci. USA 1998, 95(26), 15163–8).

Combrestatin, an active ingredient extracted from the bark of an African willow, is a potent inhibitor of neovascularisation and acts directly and selectively on the endothelium of blood vessels that have just been formed (Cancer Research, 1997, 57, 1829). This compound has recently been inserted in phase I clinical trials and later in phase II trials as an inhibitor of angiogenesis.

The curcumins, which are phenolic compounds isolated from the drug *Curcuma longa*, inhibit angiogenesis by acting directly on endothelial morphogenesis by modulating the activity of a number of proteases (Cell Growth Diff. 1998, 9(4), 305–12).

The cinnamaldehydes, compounds isolated from the bark of *Cinnamomum cassia* Blume, have shown a substantial antiangiogenic property, greater than that of other naturally occurring compounds such as genisteine with similar activity (Bioorganic and Medicinal Chemistry Letters, 1997, 7(19), 2473–6).

Despite the progress made in recent years, this sector of pharmacological research is considered by many experts in the field of medicine as one of the most promising sectors for the discovery of new drugs for the treatment of diseases characterised by abnormal angiogenesis and in particular tumours.

For these diseases, in fact, there is still a strongly perceived need for new compounds capable of blocking or interfering with the abnormal angiogenesis mechanisms which are responsible for such diseases, thus enabling cures to be found for them.

As already mentioned, such diseases include arthritic diseases, tumours, diabetic retinopathy, psoriasis, chronic inflammation and atherosclerosis.

One naturally occurring product of fungal origin, chrysanthone A, a metabolite isolated by Nasini et al. from the fungus *Ascochyta chrysanthemi* [Phytochemistry 29, 923 (1989)], has been found to possess bacteriostatic and antifungal activity. Further studies on this fungal strain have allowed the isolation of two other compounds related to chrysanthone A, and more precisely chrysanthone B and chrysanthone C, isolated by Nasini et al. [Phytochemistry Vol. 29, N°8, pp. 2499–2502 (1990)].

It has now been found that chrysanthone A, chrysanthone B and chrysanthone C are endowed with antiangiogenic activity and are therefore useful agents for the treatment of diseases characterised by abnormal angiogenesis.

The compounds according to the invention described herein are:
Chrysanthone A having Formula (I)

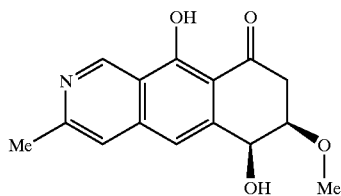
(I)

described in Phytochemistry 29, 923 (1989);
Chrysanthone B having Formula (II)

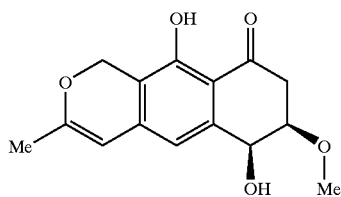
(II)

described in Phytochemistry Vol. 29, N°8, pp. 2499–2502 (1990); and
Chrysanthone C having Formula (III)

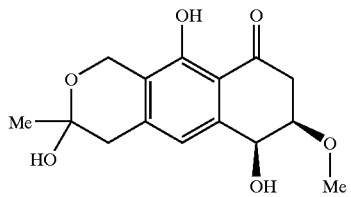
(III)

described in Phytochemistry Vol. 29, N°8, pp. 2499–2502 (1990).

The compounds according to the invention have been shown to possess antiangiogenic activity and therefore may be useful agents for the treatment of diseases characterised by abnormal angiogenesis.

One object of the invention described herein is the use of chrysanthone A, or chrysanthone B, or chrysanthone C for the preparation of a medicament with antiangiogenic activity. Another object of the invention described herein is the use of chrysanthone A, or chrysanthone B, or chrysanthone C for the treatment of tumour-type diseases.

Another object of the invention described herein is the use of chrysanthone A, or chrysanthone B, or chrysanthone C for the prevention and reduction of tumour metastases.

Another object of the invention described herein is the use of chrysanthone A, or chrysanthone B, or chrysanthone C for the treatment of arthritic diseases.

Another object of the invention described herein is the use of chrysanthone A, or chrysanthone B, or chrysanthone C for the treatment of diabetic retinopathy.

Another object of the invention described herein is the use of chrysanthone A, or chrysanthone B, or chrysanthone C for the treatment of psoriasis.

Another object of the invention described herein is the use of chrysanthone A, or chrysanthone B, or chrysanthone C for the treatment of chronic inflammatory diseases.

Another object of the invention described herein is the use of chrysanthone A, or chrysanthone B, or chrysanthone C for the treatment of atherosclerosis.

The compounds according to the invention can be obtained as described in Phytochemistry 29, 923 (1989) and Phytochemistry Vol. 29, N°8, pp. 2499–2502 (1990).

Given here below are a number of experimental data illustrating the invention.

EXAMPLE 1

Activity Tests on Chrysanthone A

The pharmacological activity of this compound was evaluated by means of predictive biological tests that reproduce the main angiogenic mechanisms in vitro. These tests are commonly used to evaluate the pro- or antiangiogenic activity of the tested compounds.

Toxicity Tests

The evaluation of the intrinsic toxicity of chrysanthone A was done by comparing it with suramin using the Sulphorhodamine B (SRB) cytotoxicity test described here below.

Bovine microvascular endothelial cells (BMEC) were seeded, at a density of 3000 cells/well, on 96-well microtiter plates, in normal culture medium (200 µl/well). On the next day the study compounds were added to the wells in scalar concentrations. On the third day after seeding the medium was removed and three washings with PBS were performed. At the end of the washings, 200 µl of culture medium were added to each well and the plates were placed in an incubator at 37° C., 5% $CO_2$ for the next 48 hours. At the end of this incubation period, the medium was removed and the cells were treated cold for 1 hour with a solution of 15% trichloroacetic acid (TCA). The wells were washed three times with distilled $H_2O$ by immersion of the plate and removal by overturning. 200 µl/well of 0.4% SRB in 1% acetic acid were added to the plates and incubated for 30 min. The wells were washed three times with 1% acetic acid, and lastly 200 µl/well of Tris 10 mM were added.

The staining of the well was quantified by spectrophotometric readout at a wavelength of 540 nm. Comparison of the values obtained in the wells containing the study compound and the controls made it possible to determine the $IC_{50}$ and $IC_0$ of the compound according to the invention, defined respectively as the concentration corresponding to 50% of cytotoxic activity ($IC_{50}$) and the maximum non-cytotoxic concentration ($IC_0$).

The results obtained and presented in Table 1 show that chrysanthone A has an $IC_{50}$ of 1.5 µM on BMEC.

Chemotaxis Test

This test is the first screening assay for compounds with potential angiogenesis inhibiting or facilitating activity (Glaser B. M. et al, Nature, 1980; 288:483–4).

Chrysanthone A, one of the compounds to which the invention relates, was subjected to a chemotaxis test using the Boyden chamber (Werner F., Goodwin R. H. and Leonard E. J., Journal of Immunology Methods, 1980; 33:239–247).

The realisation of this in-vitro assay has entailed the development of techniques for the isolation and culture of bovine endothelial cells of both the aorta (BAEC) and the adrenal marrow (BMEC) as well as the identification of suitable reference compounds. One of the advantages of the use of the Boyden chamber for the chemotaxis test is the possibility of obtaining quantitative data. The Boyden chamber consists in an upper and a lower well separated by a polycarbonate filter with 8 µm pores. A solution containing the chemoattractant is placed in the lower well, while the cells are inserted in the upper well. After a period of incubation, the cells which have migrated across the filter in response to the chemotactic stimulus are counted on the undersurface of the membrane.

In the chemotaxis test, the chemoattractant selected was bovine serum (1% in DMEM culture medium). The BMEC endothelial cells were resuspended in DMEM with 1% bovine serum albumin (BSA) and analysed in this test for 4 hours. The chemotaxis was quantified by direct cell count under the optical microscope. The migration percentages presented in the chemotaxis table expressed as "% migration" were calculated according to the formula:

$$(T-C/C) \times 100$$

where T=mean number (n°) of cells migrating in the test sample, and C=mean number of cells migrating in the control.

A control consisting of cells not treated with the study compound, migrating towards the serum, was included in every chemotaxis experiment.

The mean number of cells migrating refers to the readings of 5 microscopic fields/well in 4 independent chemotaxis wells per sample.

Normally, suramin is used as the reference compound in chemotaxis tests.

The results obtained are presented in Table 1 and show that, in two independent experiments using 0.4 μM of chrysanthone A, corresponding to the $IC_0$, the inhibition of BMEC migration was 44%±0.7 and 52%±2.8, respectively.

TABLE 1

| Name | Cytototoxicity on BMEC | | |
|---|---|---|---|
| | $IC_{50}$ | $IC_0$ | % Migration $IC_0$ |
| Suramin (reference) | >500 μM | 100 μM | 100 μM = −58 |
| Chrysanthone A | 1.5 μM | 0.4 μM | 0.4 μM = −44/−52 |

EXAMPLE 2

Activity Tests on Chrysanthone C

Toxicity Test

This test was conducted using the procedure described in Example 1.

The results obtained, presented in Table 2, show that chrysanthone C has an $IC_{50}$ of 35 μM on BMEC.

Chemotaxis Test

This test was conducted using the procedure described in Example 1.

The results obtained, presented in Table 2, show that using 10 μM of chrysanthone C, corresponding to its $IC_0$, the inhibition of BMEC migration was 54%±7.6.

TABLE 2

| Name | Cytototoxicity on BMEC | | |
|---|---|---|---|
| | $IC_{50}$ | $IC_0$ | % Migration $IC_0$ |
| Suramin (reference) | >500 μM | 100 μM | 100 μM = −58 |
| Chrysanthone A | 35 μM | 10 μM | 10 μM = −54 |

EXAMPLE 3

Cytotoxicity Tests on Human Tumour Lines with Chrysanthone A

This experiment was conducted using the toxicity test procedure described in Example 1.

The following 4 human tumour lines were tested: MCF-7; Mes-Sa; LoVo; and LoVo-Dx.

The results obtained, presented in Table 3, show that chrysanthone A is endowed with a direct cytotoxic effect on the tumour lines tested.

TABLE 3

| | $IC_{50}$ MCF-7 Line | $IC_{50}$ Mes-Sa line | $IC_{50}$ LoVo line | $IC_{50}$ LoVo-Dx line |
|---|---|---|---|---|
| Chrysanthone A | 11.6 ± 0.7 μM | 7.8 ± 0.2 μM | 15.8 ± 0.4 μM | 80 ± 4 μM |

What is claimed is:

1. A method of combating angiogenic activity in a human comprising administering to said human a chrysanthone compound selected from the group consisting of:

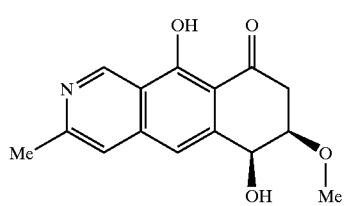

(I)

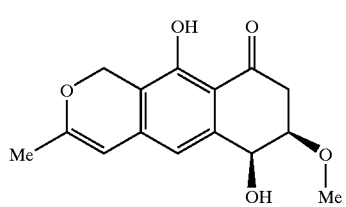

(II)

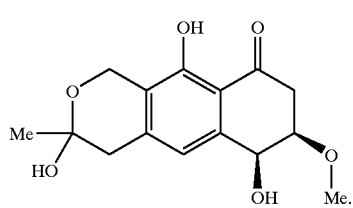

(III)

2. The method of claim 1 wherein the combating angiogenic activity is to treat a tumor disease.

3. The method of claim 1 wherein the combating angiogenic activity is to reduce or treat tumor metastases.

4. The method of claim 1 wherein the combating angiogenic activity is to treat an arthritic disease.

5. The method of claim 1 wherein the combating angiogenic activity is to treat diabetic retinopathy.

6. The method of claim 1 wherein the combating angiogenic activity is to treat psoriasis.

7. The method of claim 1 wherein the combating angiogenic activity is to treat a chronic inflammatory disease.

8. The method of claim 1 wherein the combating angiogenic activity is to treat atherosclerosis.

* * * * *